United States Patent [19]
Tu et al.

[11] Patent Number: 6,156,033
[45] Date of Patent: Dec. 5, 2000

[54] ABLATION CATHETER HAVING ELECTRODE MEANS AND METHODS THEREOF

[76] Inventors: Hosheng Tu, 2151 Palermo, Tustin, Calif. 92782; Weng-Kwen Raymond Chia, 18701 Via Palatino, Irvine, Calif. 92612

[21] Appl. No.: 09/208,182

[22] Filed: Dec. 9, 1998

Related U.S. Application Data

[60] Division of application No. 08/906,490, Aug. 5, 1997, Pat. No. 5,941,845, which is a continuation-in-part of application No. 08/856,726, May 15, 1997, Pat. No. 5,792,140.

[51] Int. Cl.$^7$ .................................................. A61B 18/18
[52] U.S. Cl. .............................. 606/41; 607/101; 607/122
[58] Field of Search .................................. 606/37–41, 49, 606/50

[56] References Cited

U.S. PATENT DOCUMENTS 5,994,715  8/1999  Goble et al. ................................ 606/41

*Primary Examiner*—Linda C. M. Dvorak
*Assistant Examiner*—Roy Gibson

[57] ABSTRACT

An improved ablation catheter with a plurality of needles on at least one electrode suitable for radiofrequency ablation of cardiac tissues includes a delivery catheter and an inner catheter. The ablation catheter has a temperature sensor and a closed-loop temperature controller. The steerable catheter having at least one electrode includes a plurality of needles, wherein a longitudinal length of said at least one electrode is 4 mm or longer, a distance of the needles of the plurality of needles on the at least one electrode is 2 mm or less, a height of the plurality of needles is 1 mm or less, and wherein the plurality of needles on the at least one electrode faces a target tissue side.

10 Claims, 5 Drawing Sheets

ABLATION CATHETER HAVING ELECTRODE MEANS AND METHODS THEREOF

This is a division of prior application Ser. No. 08/906,490, filed Aug. 5, 1997, now U.S. Pat. No. 5,941,845, which is a continuation-in-parts of Ser. No. 08/856,726 filed May 15, 1997, now U.S. Pat. No. 5,792,140.

FIELD OF THE INVENTION

The present invention generally relates to improved constructions for a cardiovascular catheter. More particularly, this invention relates to apparatus and methods for ablating cardiac arrhythmias via a steerable ablation catheter having a plurality of needles on at least one electrode for ablating intracardiac tissues resulting in a plurality of deeper and larger lesions in the myocardium or epicardium of the heart.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart. The heart includes a number of normal pathways which are responsible for the propagation of electrical signals from upper to lower chamber necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols which have proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in order to ablate the tissue of arrhythmogenic site or the accessory pathway. By successfully destroying that tissue, the abnormal signal patterns responsible for the tachycardia may be eliminated. However, in the case of atrial fibrillation (AFib), multiple arrhythmogenic sites and/or multiple accessory pathways exist. The conventional catheter with a single ablation tip electrode can not effectively cure the symptoms.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year is AFib-related.

A catheter utilized in the radiofrequency ablation is inserted into a major vein or artery, usually in the neck or groin area. The tip section of a catheter is referred to here as the portion of that catheter shaft containing the electrode or electrodes which may be deflectable. The catheter is then guided into the appropriate chamber of the heart by appropriate manipulation through the vein or artery. The tip of a catheter must be manipulatable by a physician from the proximal end of the catheter, so that the electrode at the tip section can be positioned against the tissue site to be ablated. The catheter must have a great deal of flexibility in order to follow the pathway of major blood vessels into the heart. It must permit user manipulation of the tip even when the catheter body is in a curved and twisted configuration. The tip section of a conventional electrophysiology catheter that is deflectable usually contains one large electrode about 4 mm in length for ablation purpose. The lesion is generally not deep because of a flat contact surface.

After the exact location of a target tissue is identified, the ablation apparatus may still not easily approach the target site even with assistance of an internal viewing means, such as an endoscope. This viewing situation may turn into a nightmare when an endoscope approach becomes prohibitive or unavailable during procedures. An external ultrasonic imaging capability therefore becomes in need so that ablation is not taking place in an inappropriate location. In the U.S. Pat. No. 4,794,931, there has been disclosed a catheter apparatus and system which can be utilized for ultrasonic imaging. However, there is no disclosure to how such an apparatus and system can be utilized in conjunction with an endocardial ablation apparatus having electrodes comprising a plurality of needles on at least one electrode to achieve the desired ultrasonic imaging and ultimately the desired ablation.

Imran in U.S. Pat. No. 5,281,218 teaches a needle electrode attached on a catheter for radiofrequency ablation. Though a needle like electrode is beneficial to ablate a tissue point for deep lesion, it is not possible to make a plurality of deeper and larger lesions in a region such as in the case of atrial fibrillation or in the case of epicardial side of the myocardium. For atrial fibrillation treatment, the limitation of said technique is obvious because of its single ablation point.

While a radiofrequency electrophysiology ablation procedure using an existing catheter has had promising results, the tip section of a known catheter usually have only one large electrode or one needle electrode for ablation purpose. Therefore there is a need for a new and improved catheter for making a plurality of deeper and larger lesions in the myocardium or epicardium of the heart.

SUMMARY OF THE INVENTION

In general, it is an object of the present invention to provide an improved ablation catheter with a plurality of needles on at least one electrode which can be used in ablating the arrhythmogenic region instead of an arrhythmogenic point of a patient. This catheter is particularly useful for treating the patient with atrial fibrillation (AFib) indications. In one embodiment, an ablation catheter comprises a delivery catheter having a distal end, a proximal end and at least one lumen extending therebetween. A handle is attached to the proximal end of said delivery catheter.

The delivery catheter has an electrode deployment means. The electrode deployment means includes a retractable inner catheter having a tip section, comprising a plurality of needles on at least one electrode. The inner catheter comprises a distal end, a proximal end, and a central lumen extending therebetween. The proximal end is attached to the electrode deployment means which has a push-pull type mechanism on the handle. In one embodiment, the at least one electrode becomes the tip electrode while a plurality of band electrodes spaced at a pre-determined distance from the preceding electrode. In an alternate embodiment, the at least one electrode contains a plurality of needles on said electrode. In a further embodiment, the plurality of needles on at least one electrode faces outward toward the tissue surface to be ablated. Therefore, at ablation time, the needles are positioned essentially perpendicular to the tissues to be ablated. In still another embodiment, the needles face at different directions so as to contact the endocardial tissue when a bi-directional deflectable catheter is used in the ablation procedure. The inner catheter has a non-deployed state when it is positioned in the delivery catheter. This non-deployed state is maintained during the ablation catheter insertion operation into a patient and during withdrawal of the catheter from a patient.

The ablation catheter further comprises a steering mechanism at the handle for controlling the deflection of said at least one electrode. Usually a rotating ring or a push-pull plunger is employed in the steering mechanism. In another embodiment, the steerable ablation catheter comprises a bidirectional deflection of the tip section having a plurality of needles on the at least one electrode. One end of the steering wire is attached at certain point of the tip section of said inner catheter. The other end is attached to the steering mechanism at the handle. The steering mechanism on a steerable catheter or device is well known to those who are skilled in the art.

The inner catheter has a deployed state when it is advanced out of the distal end of said delivery catheter. Deployment of the inner catheter is accomplished by a pushing action on the push-pull deployment mechanism at the handle. In one embodiment, the tip section of the deployed inner catheter has a preformed shape so that the at least one electrode would extend outwardly of the delivery catheter when deployed. The degree of deployment is controlled by the pushing action at said push-pull mechanism on the handle and is proportional to the push distance on the push-pull plunger of the push-pull mechanism which is quantifiable.

The deployed inner catheter having the at least one electrode, defines an ablation target. The sharp point of the needles of each electrode is positioned at the forward side facing the target tissue. After finishing the ablation operation, the retraction of the inner catheter is accomplished by pulling back the inner catheter relative to the delivery catheter. The degree of retraction is mainly controlled by the pulling action at the push-pull mechanism on the handle.

At least one conducting wire which is soldered to the electrode passes through the lumen of the inner catheter and the interior void of the handle and is thereafter soldered to a contact pin of the connector secured at the proximal end of the handle. Therefrom, the conducting wire is connected to an external RF generator for ablation operations and/or to an EKG monitor for recording and display of the endocardial electrical signal.

In an additional embodiment, the ablation system further comprises a temperature sensing and closed-loop temperature control mechanism for the electrode having at least one temperature sensor at the tissue contact site of the electrodes. The location of the temperature sensor is preferably in the proximity of one of the needles of the electrodes.

In a particular embodiment, the length of the at least one electrode is 4 mm or longer. In an alternate embodiment, the needles on an electrode are equally spaced and the distance between the needle tip of the at least one electrode is 2 mm or less. The height of the needle is usually 1 mm or less. The material for the at least one electrode may consist of conductive metals such as platinum, iridium, gold, silver, stainless steel, Nitinol, or an alloy of their mixture.

In a still further embodiment, the tip section of the inner catheter comprising the electrodes is formed of a conducting material without catheter shaft. The at least one electrode in this embodiment is formed of a flexible metal mesh that can be retracted into the delivery catheter during inserting and withdrawal of said inner catheter system.

In order to provide increased torsional rigidity to the catheter shaft, the shaft material preferably comprises a polymeric tube having a Durometer in the range from 30D to 90D, usually from 40D to 65D. Preferably, the shaft has a composite structure including a base layer of a relatively low Durometer material, a stiffening layer, for example, metal braid or coil, and an outer layer comprising the biocompatible polymeric material or the material that may render itself biocompatible by surface treatment. To enhance biocompatibility, the catheter shaft further comprises surface coating of heparin on the surface of the catheter shaft. It is hypothesized that the coated heparin forms a barrier, while not releasing heparin from said surface, between the blood and the catheter surface to enhance biocompatibility during electrophysiology procedures. In a further embodiment, an ablation catheter further comprises surface treatment of low surface energy substrates, such as Teflon® type fluorinated polymers, to mitigate blood coagulation during high-energy ablation. Fluorinated polymer can be deposited on the shaft surface via plasma coating technology or the like.

A method for operating a steerable ablation catheter system having a plurality of needles on at least one electrode at the tip section of an deployable inner catheter within a heart chamber comprises percutaneously introducing the delivery catheter through a blood vessel to the heart chamber, wherein the at least one electrode is deployed by pushing the inner catheter forward and forming the desired electrode pre-shape; deflecting the distal section of the inner catheter about a transverse axis to position the at least one electrode near a target region on an interior wall of the heart chamber; intimately contacting the electrode, including the needles, with the intracardiac tissue; and applying radiofrequency energy to the target location through the needles of this invention.

Another object of the invention is to provide a catheter and methods in which it is possible to view the area to be ablated prior to ablation to ensure that ablation is being carried out in an appropriate location. The electrode having a plurality of needles is encoded with plurality of markers which are visible to ultrasonic energy. The markers have been provided in the form of encapsulated air bubbles. In another embodiment, probes with ultrasonic signal capability are located adjacent to the needle of said electrode. The ultrasonic signals are directed outwardly and received inwardly relative to the front side of the electrode to permit rapid and substantially continuous viewing of the target tissue.

The method and apparatus of the present invention have several significant advantages over known catheter or ablation techniques. In particular, the at least one electrode having a plurality of needles of a steerable ablation catheter of this invention may result in a plurality of deeper, larger and contiguous lesions which is highly desirable in the AFib treatment.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF EXEMPLARY EMBODIMENTS

Figure 1:
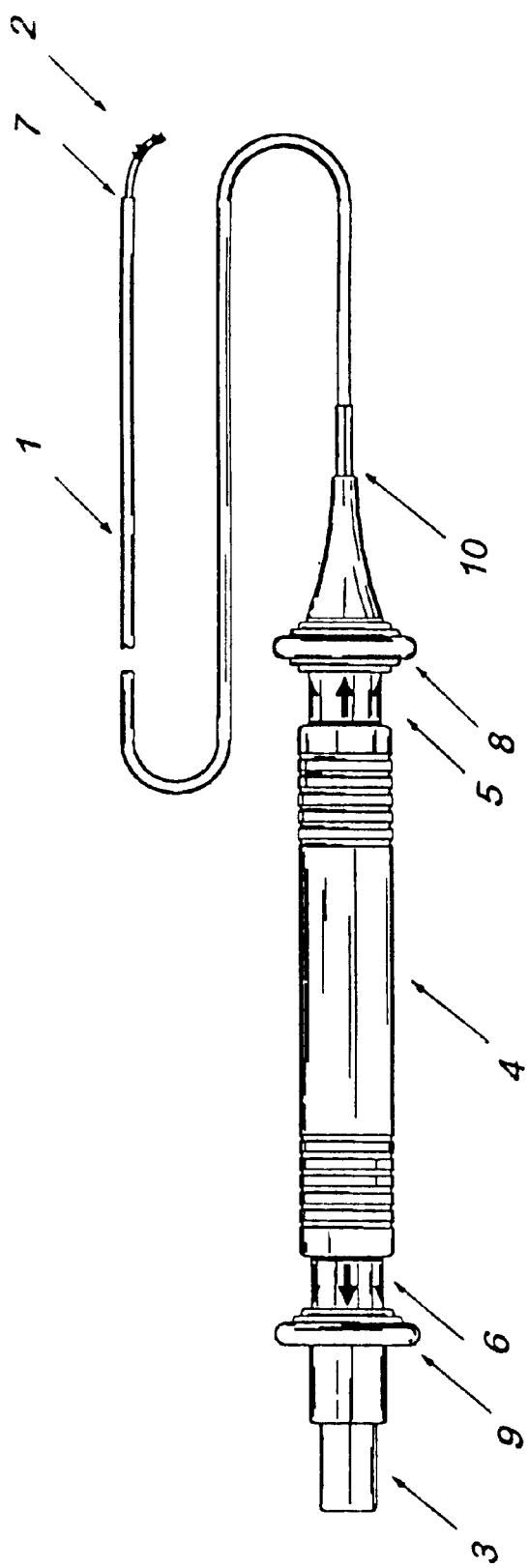
FIG. 1 is an overall view of a catheter having at least one electrode comprising a plurality of needles constructed in accordance with the principles of the present invention.

FIG. 1 shows a perspective view of the catheter having a delivery catheter. An ablation catheter constructed in accordance with the principles of the present invention comprises a delivery catheter 1 having a distal end 7, a proximal end 10, and at least one lumen therebetween. The delivery catheter comprises an electrode deployment means, wherein the deployment means comprises a retractable inner catheter 2 having a tip section, comprising a plurality of needles on at least one electrode. A handle 4 is attached to the proximal end 10 of said delivery catheter 1.

The connector 3 secured at the proximal end of the catheter is part of the handle section 4. The handle has one steering mechanism 5 and one inner catheter deployment mechanism 6. The steering mechanism 5 is to deflect the tip section of the inner catheter 2 when the tip section is deployed outside of the distal end 7 of said delivery catheter 1. By pushing the front plunger 8 of the handle 4, the tip section of the inner catheter deflects to one direction. By pulling the front plunger 8, the tip section returns to its neutral position.

The deployment mechanism 6 constitutes a catheter shaft for the inner catheter, wherein the catheter shaft resists buckling inside the delivery catheter 1 and inside the cavity of the handle 4. The rear plunger 9 is used to push the tip section of the inner catheter 2 outwards of the delivery catheter 1 for ablation purpose. While the catheter is introduced into the body or removed from the body, the tip section of the inner catheter 2 is retracted into the delivery catheter 1 by pulling back the rear plunger 9.

Figure 2:
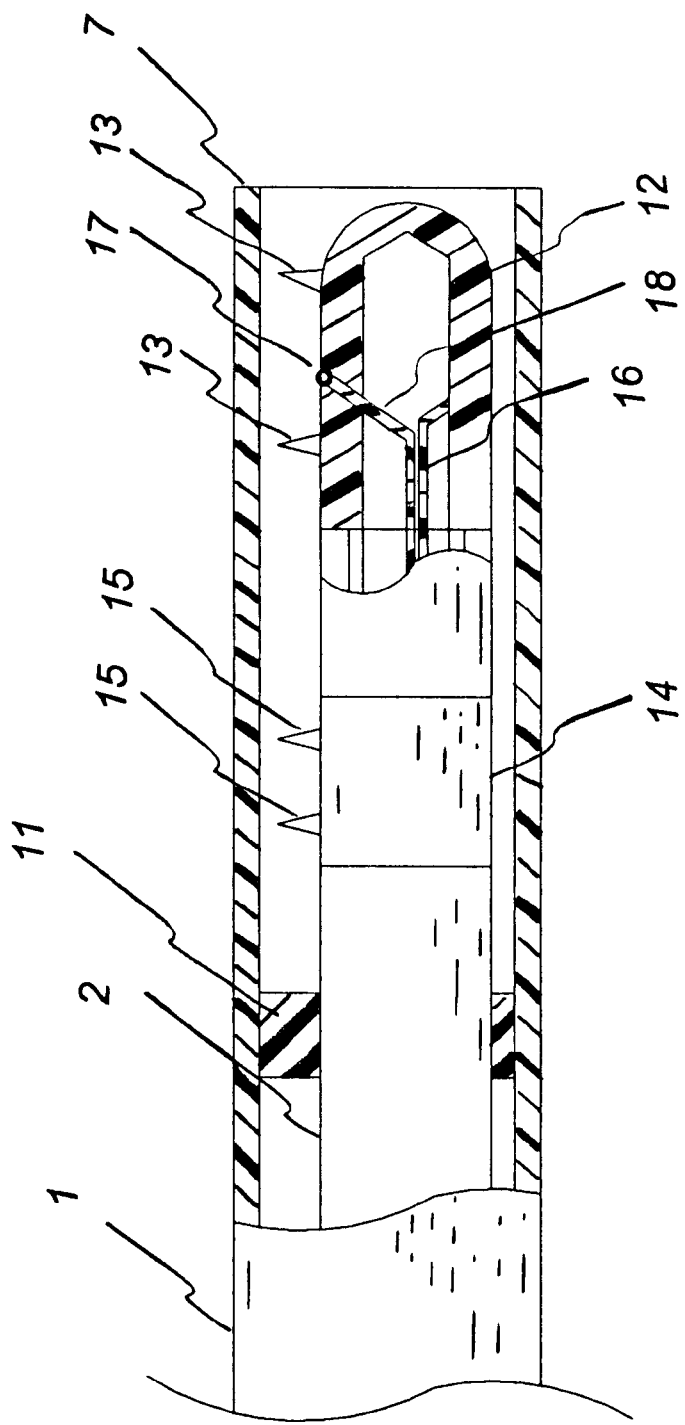
FIG. 2 is a close-up view of the distal section of the catheter at non-deployed state.

FIG. 2 shows a close-up view of the distal section of the catheter at non-deployed state of FIG. 1. The tip section of the delivery catheter comprises a distal end 7 and a sealable opening 11. The tip section of the inner catheter 2 comprises a tip electrode 12 which has a plurality of needles 13, and at least one band electrode 14 which has a plurality of needles 15. The electrodes are formed of a conducting material. In one embodiment, at least one electrode is a metal mesh securely wrapped outside of the catheter shaft of the inner catheter 2, wherein the electrode has a plurality of needles 14 or 15.

Figure 3:
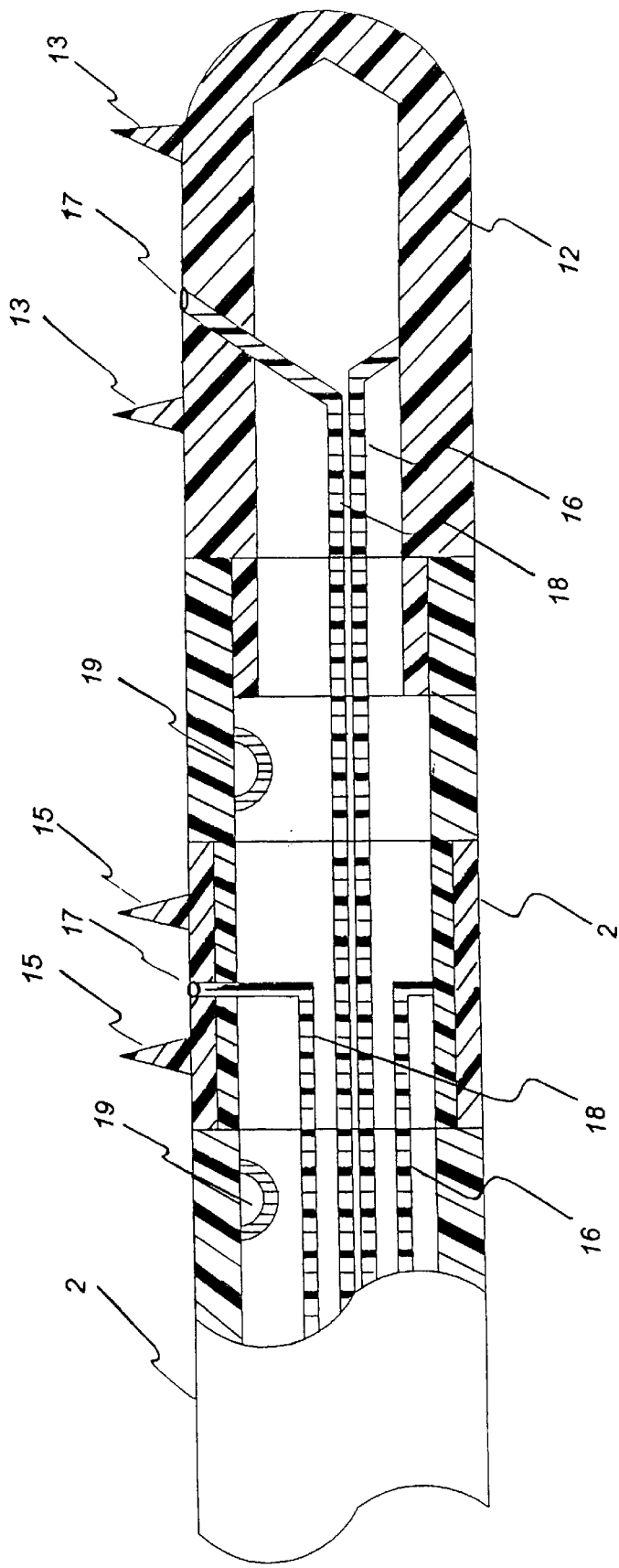
FIG. 3 is a cross-sectional view of the tip section of the inner catheter having at least one electrode comprising a plurality of needles.

FIG. 3 shows a cross-sectional view of the tip section with at least one temperature sensor 17 and ultrasonic imaging capabilities. In order to enhance the ablation positioning of said ablation catheter; the electrode is encoded with markers 19 which are visible to ultrasonic energy. Such markers 19 are provided in the form of encapsulated air bubbles. Several markers 19 are placed on the same side of the needles and in the proximity of the needles 15 of the at least one electrode 14 in a way so that the exact location of the needles 15 is visible to an external ultrasonic energy. By way of example, the bubble in a marker can be formed by introducing air by a syringe (not shown) penetrating the wall of the plastic front body of said electrode and thereafter is sealed by epoxy.

The at least one electrode comprising a plurality of needles has an insulated conducting wire 16 which passes through the lumen of the inner catheter 2 and is soldered to a contact pin of the connector 3 at the proximal end of the handle 4. The conducting wire from the connector end is externally connected to an EKG for diagnosis or to a RF current generator during an electrophysiology ablation procedure. Therefrom, the RF energy is transmitted through the conducting wire to the at least one electrode and delivered the energy to the target tissue.

A temperature sensor 17, either a thermocouple or a thermister, is constructed at the proximity of one needle 13 or 15 of the electrodes 12 or 14 to measure the tissue contact temperature when RF energy is delivered. The temperature sensing wire 18 from the thermocouple or thermister is connected to one of the contact pins (not shown) of the connector 3 and externally connected to a transducer and to a temperature controller. The temperature reading is thereafter relayed to a close-loop control mechanism to adjust the RF energy output. The RF energy delivered is thus controlled by the temperature sensor reading or by the preprogrammed control mechanism.

The tip section having a plurality of needles on the at least one electrode formed of conducting material can be extended out of the delivery catheter 1 and retracted into said delivery catheter by a deployment mechanism 6 at the handle 4. To prevent blood from backflow into the delivery catheter 1, a silicone type sealer 11 is installed at certain opening of the delivery catheter between the delivery catheter 1 and the inner catheter 2.

Figure 4:
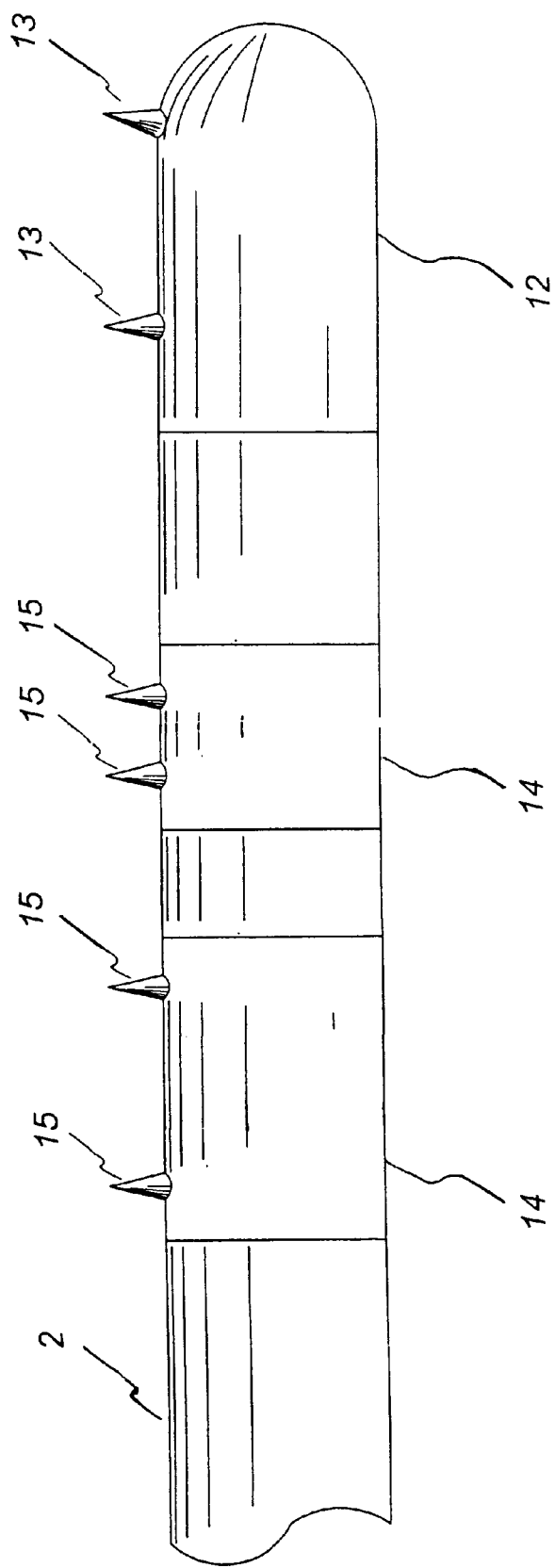
FIG. 4 is a perspective view of the tip section of the inner catheter of FIG. 1.

FIG. 4 shows a perspective view of the tip section of the inner catheter, wherein the tip section comprises a plurality of electrodes having a plurality of needles secured onto the electrode. For the steering mechanism 5, a steering wire is firmly attached onto a flat wire or coil spring (not shown) at the distal contact point of said flat wire. The proximal end of the steering wire is secured to the push-pull plunger 8 of the steering mechanism. By pushing or pulling the steering wire from the handle, the distal portion of the inner catheter 2 deflects to one direction.

Figure 5:
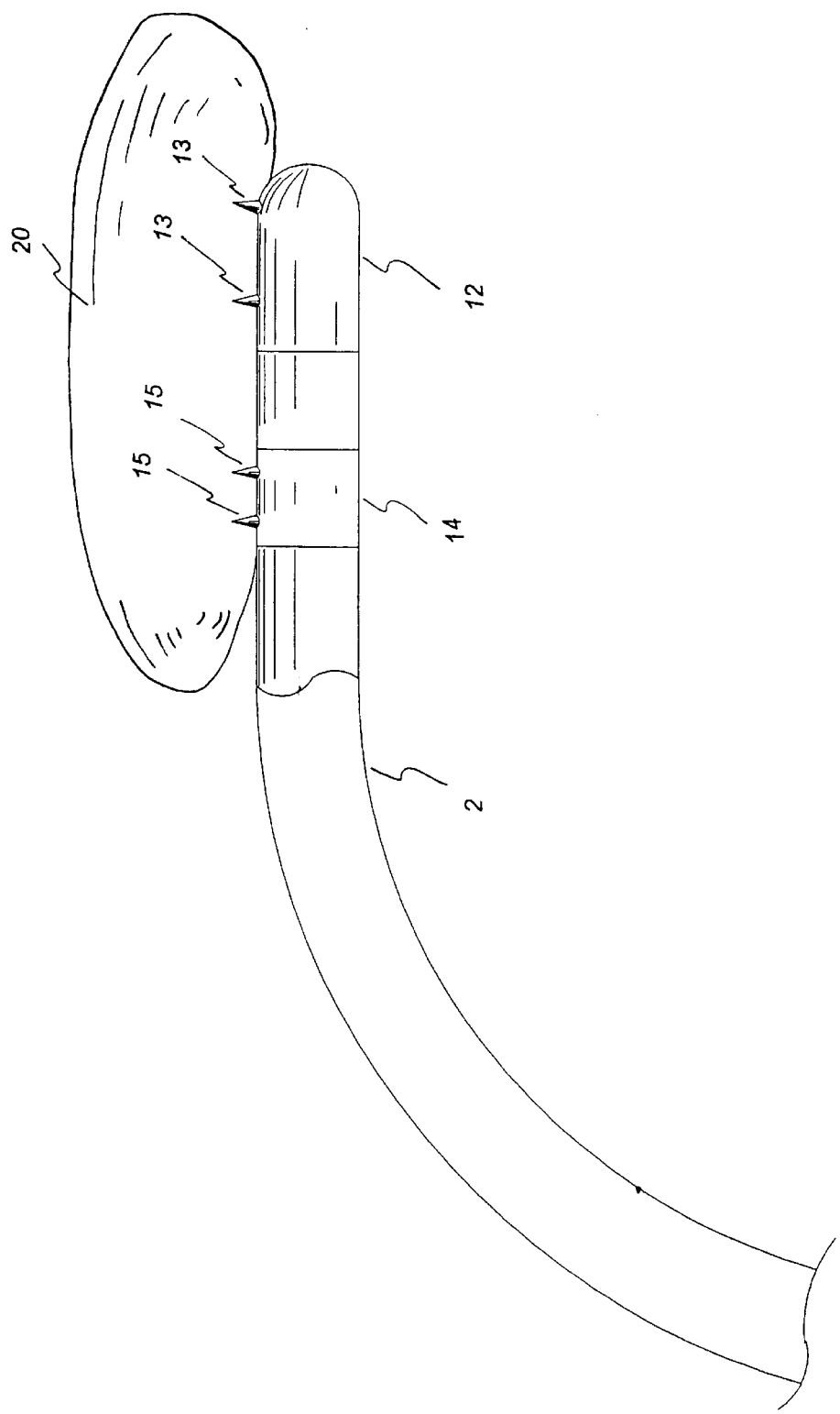
FIG. 5 shows the contact of the at least one electrode of the catheter of this invention with the tissue.

FIG. 5 shows the contact of the needles 13 and 15 of the at least one electrodes 12 and 14 with the target tissue 20.

The needle may contact the tissue at an angle essentially perpendicular to the target tissue. RF energy is applied thereafter and a plurality of deep and large lesions are created which are contiguous for the treatment of a tachycardia.

From the foregoing, it should now be appreciated that an improved ablation catheter having a plurality of needles on the at least one electrode and a steerable mechanism has been disclosed for ablation procedures, including endocardial and body tissue ablations. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. An ablation catheter comprising:
   a delivery catheter having a distal end, a proximal end, and at least one lumen extending between the distal end and the proximal end;
   a handle attached to the proximal end of the delivery catheter;
   an inner catheter located within the at least one lumen of the delivery catheter, the inner catheter having a distal tip section, a distal end, a proximal end, and a central lumen extending between the distal end and the proximal end of the inner catheter, wherein the distal tip section having at least one electrode; and
   a plurality of needles on the at least one electrode, each having a tip, wherein a longitudinal length of said at least one electrode is 4 mm or longer, a distance between the tips of the needles is 2 mm or less, a height of each needle is 1 mm or less, and wherein the plurality of needles on the at least one electrode face a target tissue side.

2. An ablation catheter as in claim 1 further comprising a steering mechanism at the handle for controlling deflection of the ablation catheter.

3. An ablation catheter as in claim 2, wherein the plurality of needles on the at least one electrode is formed of a metal mesh.

4. An ablation catheter as in claim 2 further comprising a closed-loop temperature control mechanism and at least one temperature sensor mounted on the at least one electrode and adapted for providing sensing signals for the closed-loop temperature control mechanism.

5. An ablation catheter as in claim 2, wherein the needles on the at least one electrode is made of a material selected from the group of platinum, iridium, gold, silver, stainless steel, and Nitinol.

6. An ablation catheter as in claim 2 further comprising a coating of heparin on an exterior surface of the inner catheter to enhance biocompatibility.

7. An ablation catheter as in claim 2 further comprising a treatment on an exterior surface of the inner catheter with low surface energy substrates of fluorinated polymers to mitigate blood coagulation.

8. An ablation catheter as in claim 2 further comprising ultrasonic probes on a same side of the needles on the at least one electrode adapted for ultrasonic signals being directed outwardly and received inwardly relative to the at least one electrode to permit rapid and substantially continuous viewing of a target tissue.

9. An ablation catheter as in claim 2 further comprising a plurality of ultrasonic visible markers being disposed in close proximity to the plurality of needles on the at least one electrode.

10. A tissue ablation system using an ablation catheter comprising:
    a delivery catheter having a distal end, a proximal end, and at least one lumen extending between the distal end and the proximal end;
    a handle attached to the proximal end of the delivery catheter;
    an inner catheter located within the at least one lumen of the delivery catheter, the inner catheter having a distal tip section, a distal end, a proximal end, and a central lumen extending between the distal end and the proximal end of the inner catheter, wherein the distal tip section having at least one electrode;
    a plurality of needles on the at least one electrode, each having a tip, wherein a longitudinal length of said at least one electrode is 4 mm or longer, a distance between the tips of the needles is 2 mm or less, a height of each needle is 1 mm or less, and wherein the plurality of needles on the at least one electrode face a target tissue side; and
    a RF current generator, wherein a RF current is delivered from the RF current generator to the plurality of needles on the at least one electrode.

* * * * *